(12) United States Patent
Minagi et al.

(10) Patent No.: US 7,690,258 B2
(45) Date of Patent: Apr. 6, 2010

(54) BURIED PIPE EXAMINING METHOD

(75) Inventors: Takushi Minagi, Shiga (JP); Hiroshi Iida, Shiga (JP); Masanori Asano, Shiga (JP); Toshiro Kamada, Osaka (JP)

(73) Assignees: Sekisui Chemical Co., Ltd., Osaka (JP); Gifu University, Gifu (JP)

( * ) Notice: Subject to any disclaimer, the term of this patent is extended or adjusted under 35 U.S.C. 154(b) by 456 days.

(21) Appl. No.: 11/658,658

(22) PCT Filed: Jul. 26, 2005

(86) PCT No.: PCT/JP2005/013655

§ 371 (c)(1),
(2), (4) Date: Jan. 26, 2007

(87) PCT Pub. No.: WO2006/011484

PCT Pub. Date: Feb. 2, 2006

(65) Prior Publication Data

US 2008/0314151 A1 Dec. 25, 2008

(30) Foreign Application Priority Data

Jul. 26, 2004 (JP) ............................. 2004-217832
Jul. 26, 2004 (JP) ............................. 2004-217833

(51) Int. Cl.
*G01N 29/04* (2006.01)
*G01N 29/46* (2006.01)

(52) U.S. Cl. ...................... 73/592; 73/11.01; 73/12.08; 73/659; 73/865.8

(58) Field of Classification Search .................. 73/592, 73/579, 584, 597, 599, 600, 622, 659, 660, 73/11.01, 12.08, 865.8

See application file for complete search history.

(56) References Cited

U.S. PATENT DOCUMENTS 3,302,453 A * 2/1967 Wood et al. .................... 73/622
4,581,196 A * 4/1986 Sakagami et al. ........... 376/216

(Continued)

FOREIGN PATENT DOCUMENTS

JP 09-269215 10/1997

(Continued)

*Primary Examiner*—Hezron Williams
*Assistant Examiner*—J M Saint Surin
(74) *Attorney, Agent, or Firm*—Cheng Law Group, PLLC

(57) ABSTRACT

An impact elastic wave test is conducted to measure propagating waves in a pipe to be examined, a frequency spectrum of the propagating waves is analyzed, and at least a spectral area value in a first frequency region and a spectral area value in a second frequency region of the frequency spectrum are evaluated, thereby determining a type of a deteriorated state of the buried pipe. A correlation relationship between a parameter obtained from a force-deformation relationship indicating a relationship between a force externally input to a sample pipe and a deformation of the sample pipe due to the force, and impact elastic wave test data obtained by conducting an impact elastic wave test with respect to the sample pipe is previously obtained, an impact elastic wave test is conducted with respect to a pipe to be examined to collect impact elastic wave measurement data of the pipe to be examined, and the actually measured impact elastic wave measurement data is evaluated based on the correlation relationship, thereby quantitatively determining a degree of deterioration of the pipe to be examined.

4 Claims, 14 Drawing Sheets

U.S. PATENT DOCUMENTS

| | | | |
|---|---|---|---|
| 5,540,096 A * | 7/1996 | Woodcock et al. | 73/579 |
| 5,544,074 A * | 8/1996 | Suzuki et al. | 702/51 |
| 5,563,848 A * | 10/1996 | Rogers et al. | 367/99 |
| 6,003,376 A * | 12/1999 | Burns et al. | 73/584 |
| 6,667,709 B1 * | 12/2003 | Hansen et al. | 342/22 |
| 7,360,462 B2 * | 4/2008 | Nozaki et al. | 73/865.8 |
| 7,426,879 B2 * | 9/2008 | Nozaki et al. | 73/865.8 |
| 7,530,270 B2 * | 5/2009 | Nozaki et al. | 73/597 |

FOREIGN PATENT DOCUMENTS

| | | |
|---|---|---|
| JP | 10-142200 | 5/1998 |
| JP | 2006-038597 | 2/2006 |
| JP | 2006-038598 | 2/2006 |

* cited by examiner crack introducing method

⇧ input position    ☐ reception position

BURIED PIPE EXAMINING METHOD

TECHNICAL FIELD

The present invention relates to a method for examining a deteriorated state of a buried pipe.

BACKGROUND TECHNOLOGY

Number of accidents such as cave-ins, water leakages, and the like, of sewer pipelines and agricultural pipelines is increasing year by year due to corrosion and abrasion or breakage of aging buried pipes. Therefore, there is a demand for appropriate diagnosis of the degree of pipe deterioration, and repair/replacement based on the result of the diagnosis.

In order to diagnose for sewer pipelines and agricultural pipelines, it is generally necessary to put elemental zones constituting an exploration range in order of deterioration level, and find quantitative deterioration p levels, so as to prioritize repair/reconstruction works and determine work methods.

Therefore, conventionally, external appearance is generally checked by visual inspection or a CCTV camera, and if necessary, a core is extracted and a physical property is examined. With such a method, however, only a deterioration which is visually perceived can be detected, a deterioration in the outer circumference or inside of a pipe fails to be found. Therefore, it is difficult to quantitatively detect a deterioration phenomenon as appropriate. It is also necessary to extract a large amount of core so as to collect quantitative data, so that the strength of a sewer pipeline or an agricultural pipeline is impaired, or much time and effort are required to conduct work.

Examination methods for concrete structures may be applicable. For example, a system for estimating a width and a depth of a crack using elastic waves has been proposed (see, for example, Patent Document 1 and Patent Document 2). However, since this examination system utilizes a reduction in the propagation energy of elastic waves or the counted number of elastic waves (the counted number of amplitudes exceeding a predetermined value), the system is easily affected by a situation surrounding a buried pipe, resulting in poor examination accuracy.

Patent Document 1: JP H10-142200 A
Patent Document 2: JP H09-269215 A

DISCLOSURE OF INVENTION

Problem to be Solved by the Invention

The present invention is provided to solve the above-described problems. An objective of the present invention is to provide a buried pipe examining method capable of examining a type of a deterioration phenomenon and a degree of deterioration in a buried pipe constituting a sewer pipeline, an agricultural pipeline or the like, without being affected by environments where the pipe is buried and with high accuracy.

Means for Solving Problem

A buried pipe examining method of the present invention is a method for examining a deteriorated state of a buried pipe from inside of the pipe, wherein an impact elastic wave test is conducted to measure propagating waves in the pipe to be examined, a frequency spectrum of the propagating waves is analyzed, and a deterioration phenomenon type is determined based on at least a spectral area value in a first frequency region and a spectral area value in a second frequency region of the frequency spectrum.

In the buried pipe examining method of the present invention, an exemplary technique of setting a frequency region in which a spectral area value is calculated is a technique in which an impact elastic wave test is conducted with respect to each of a plurality of types of sample pipes having different states to measure propagating waves, a frequency spectrum of the propagating waves of each sample pipe is analyzed, each frequency spectrum is integrated every a predetermined small frequency region, resultant integrals are successively summed to obtain a sum of the integrals, and a frequency at a point where the sum of the integrals changes significantly is determined, thereby setting the frequency region in which the spectral area value is obtained.

In the buried pipe examining method of the present invention, the frequency region in which the spectral area value is obtained preferably includes the first frequency region having a start point in the range of 0 to 2.5 kHz and an end point in the range of 3 to 5.5 kHz, and the second frequency region having the same start point as that of the first frequency region and an end point in the range of 7 to 10 kHz.

Hereinafter, the present invention will be described in detail.

The present applicants propose a technique of conducting an impact elastic wave test with respect to a pipe, such as a reinforced-concrete pipe or the like, to measure waves propagating through the pipe, analyzing a frequency spectrum of the propagating waves, and determining a deteriorated state of the pipe based on the frequency spectrum.

In the present invention, the following was found. The frequency spectrum thus obtained by the impact elastic wave test is integrated every a predetermined small frequency region, and the resultant integrals are successively summed to obtain the sum of the integrals (spectral area value). In this case, there is a point where the sum of the integrals changes significantly. In addition, the phenomenon that such a change point occurs has a relationship with a "crack in an axial direction of a pipe", a "crack in a circumferential direction", a "reduction in pipe wall thickness", or the like, as indicated in a graph of FIG. 10.

Such a phenomenon is utilized in the present invention. As described above, an impact elastic wave test is conducted to measure waves propagating through a pipe to be examined. A frequency spectrum of the propagating waves is analyzed to evaluate a spectral area value of a first frequency region (e.g., 0.5 to 4 kHz) of the frequency spectrum and a spectral area value of a second frequency region (e.g., 0.5 to 10 kHz), thereby specifying whether a type of the deterioration phenomenon of the pipe to be examined is "sound", "axial crack", "circumferential crack", "axial+circumferential crack", or "pipe wall thickness reduction".

Next, a method for setting a frequency region used when a spectral area is obtained in the present invention will be described.

As a plurality of types of sample pipes having different states (deteriorated states), a "sound pipe", an "axial crack-introduced pipe", a "circumferential crack-introduced pipe", an "axial+circumferential crack-introduced pipe", and a "wall thickness-reduced pipe" are prepared. These sample pipes are each subjected to an impact elastic wave test. The resultant propagating waves are measured and the frequency spectrum of the propagating waves of each pipe is analyzed.

Next, the frequency spectrum of each pipe is integrated every a predetermined small frequency region (e.g., 0.5 kHz), and the resultant integrals are successively summed to obtain the sum of the integrals. The sum of the integrals thus obtained for each pipe is plotted on a graph where the frequency is a parameter. As a result, a graph as shown in FIG. 10 is obtained. Note that the graph of FIG. 10 is obtained by modeling the results of impact elastic wave tests on samples S1 to S5 described below.

The graph of FIG. 10 will be discussed. The sums of integrals for the pipes until a frequency region F1 including a point where the sum of integrals of the "axial crack-introduced pipe" changes significantly are divided into two groups: a first group having a large sum of integrals (the "sound pipe", the "wall thickness-reduced pipe", and the "axial crack-introduced pipe"); and a second group having a small sum of integrals (the "circumferential crack-introduced pipe" and the "axial+circumferential crack-introduced pipe"). Note that the reason why the "wall thickness-reduced pipe" has a larger sum of integrals than that of the "sound pipe" in the first group is that a smaller pipe wall thickness provides a larger amount of low frequency components.

Further, the sum of integrals until a frequency region F2 including a point where the sum of integrals of the "wall thickness-reduced pipe" changes significantly (decrease) and a point where the sum of integrals of the "circumferential crack-introduced pipe" changes significantly (increase), is slightly larger for the "sound pipe" than for the "wall thickness-reduced pipe", is extremely smaller for the "axial crack-introduced pipe" than for the "sound pipe" and the "wall thickness-reduced pipe", and is larger for the "circumferential crack-introduced pipe" than for the "axial+circumferential crack-introduced pipe".

Therefore, the deterioration phenomenon type can be determined by using the frequency region F1 including a point where the sum of integrals of the "axial crack-introduced pipe" changes significantly, as the first frequency region, and the frequency region F2 including a point where the sums of integrals of the "wall thickness-reduced pipe" and the "circumferential crack-introduced pipe" change significantly, as the second frequency region.

Specifically, the "sound pipe" is used as a reference. The sum of integrals (spectral area) in the first frequency region is considered to be "large" when it is larger than that of the "sound pipe", "intermediate" when it is about the same as or slightly, smaller than that of the "sound pipe", and "small" when it is extremely smaller than that of the "sound pipe". The sum of integrals (spectral area) in the second frequency region is considered to be "large" when it is about the same as or slightly smaller than that of the "sound pipe", "intermediate" when it is smaller than that of the "sound pipe", and "small" when it is extremely smaller than that of the "sound pipe". In this case, the deterioration phenomenon type is determined under a criterion indicated in Table 2 described below.

Note that the number of frequency regions in which a spectral area value is obtained is not limited to two (i.e., the above-described first and second frequency regions), and may be three or more.

An examination method of the present invention is also a method for examining a deteriorated state of a buried pipe from inside of the pipe, wherein a correlation relationship between a parameter obtained from a force-deformation relationship indicating a relationship between an external force input to a sample pipe and a deformation of the sample pipe due to the force, and impact elastic wave test data obtained by conducting an impact elastic wave test with respect to the sample pipe is previously obtained, an impact elastic wave test is conducted with respect to a pipe to be examined to collect impact elastic wave measurement data of the pipe to be examined, and the actually measured impact elastic wave measurement data is evaluated based on the correlation relationship between the parameter obtained from the force-deformation relationship and the impact elastic wave test data, thereby quantitatively determining a degree of deterioration of the pipe to be examined.

In the present invention, a load-displacement curve or a stress-strain curve may be used as parameter obtained from the force-deformation relationship of the sample pipe.

Also, an angle ratio of slope of a load-displacement curve or a stress-strain curve may be used as the parameter obtained from the force-deformation relationship.

In the present invention, preferably, an impact elastic wave test is conducted to measure propagating waves in a pipe, a frequency spectrum of the propagating waves is analyzed, and an area ratio of low frequency components to a predetermined frequency region of the frequency spectrum is used as the impact elastic wave test data and the actually measured impact elastic wave data.

Hereinafter, the present invention will be described in detail.

The rigidity of a pipe, such as a reinforced-concrete pipe or the like decreases if a crack occurs in the pipe. As a method for evaluating the pipe rigidity, there is generally a known method for measuring a force-deformation curve, such as a load-displacement curve (or a stress-strain curve) or the like. As another method, there is an impact vibration test. According to the present invention, it was found that there is a correlation between such a force-deformation curve and the result of measurement of the impact elastic wave test (the detail will be described below). As described above, the present invention is characterized in that a correlation relationship between a force-deformation curve and test data of an impact elastic wave test is previously obtained, and actual impact elastic wave measurement data obtained when an impact elastic wave test is conducted with respect to a pipe to be examined (existing buried pipe) is evaluated based on the correlation relationship between the force-deformation curve and the test data of the impact elastic wave test, thereby quantitatively determining the degree of deterioration of the pipe to be examined.

Here, in the present invention, as a specific test method used to obtain a correlation between a force-deformation curve and test data of an impact elastic wave test, for example, a method is employed which conducts a loading test in which a displacement (or a strain) is occurred when a line load is applied to a pipe is measured to obtain a load-displacement curve (or a stress-strain curve), and an impact elastic wave test (described below) which is conducted during the load-displacement measurement process while removing a line load on the pipe every a predetermined step.

Impact Elastic Wave Test

In the present invention, an impact elastic wave test with respect to a sample pipe and a pipe to be examined is conducted as follows.

[Input Method]

As an input device, an impact tool, such as a hammer, a steel ball, an impulse hammer or the like, can be used. Since it is desirable that the same force be invariably applied by impact, a method of swinging a hammer, a steel ball or the like with a constant force using a Schmidt hammer, a spring, a piston or the like, or a method of dropping a steel ball or the like from a constant height, is desirable, for example. When an impulse hammer is used, it is desirable that numerical data of input information be previously measured so as to be able to be reflected during analysis.

Particularly, as an input device used when a maximum peak strength is evaluated, for example, an impact tool capable of converting input information into numerical values (e.g., an impulse hammer), or an impact tool capable of impact with a constant force, is desirable.

[Reception Method]

As a reception device, an acceleration sensor, an AE sensor, a vibration sensor, or the like can be used. As a method of setting the reception device, the device may be fixed using a tape, an adhesive or the like, or may be attached by a hand, a pressing jig or the like.

Since these input device and reception device may contact water, acidic water or basic water, it is desirable that the devices be made of a material highly resistant to corrosion, such as stainless steel or the like.

[Measurement Method]

An impulse hammer or the like is used to input elastic waves to an inner surface of a pipe. A reception device set in the pipe is used to measure waves propagating through the pipe, and a waveform is stored by a recording device (measurement of reception data). The input position and the position of the reception device are desirably placed and separated by ¼ or more of a length of a pipe to be examined. This is because it is easy to detect a change in a vibration phenomenon of the whole pipe due to a deterioration, such as a crack or the like. It is also desirable that the input position and the reception position be set at the same relative position.

[Calculation of Low Frequency Area Ratio]

For example, there are two calculation methods as follows.

(1) Measured waveform data is subjected to FFT to draw a frequency spectrum. For the frequency spectrum distribution, an area ratio of low frequency components to a predetermined frequency region (low frequency area ratio=[the area of low frequency components (e.g., 0 to 5 kHz)]/[the area of predetermined-region components (e.g., 0 to 10 kHz)], is obtained.

(2) For measured input and reception data, a frequency spectrum is drawn, taking into consideration a relationship between an input (impact side) and an output (reception side). For the frequency spectrum distribution, an area ratio of low frequency components to a predetermined frequency region (low frequency area ratio=[the area of low frequency components (e.g., 0 to 5 kHz)]/[the area of predetermined-region components (e.g., 0 to 10 kHz)], is obtained. When the analysis method of (2) is employed, an impact force (input information) of an impulse hammer needs to be converted into a numerical value. Here, for example, the frequency spectrum in view of the relationship between an input and an output is represented by $H(f)=B(f)/A(f)$ where $A(f)$ represents a Fourier spectrum of the input, $B(f)$ represents a Fourier spectrum of the output, and $H(f)$ represents a transfer function (frequency response function). $H(f)$ draws a distribution of the frequency spectrum.

In the present invention, a correlation between the load-displacement curve obtained by the loading test and the low frequency area ratio obtained by the impact elastic wave test is obtained. For example, a relationship [the low frequency area ratio]-[the angle ratio of slope of the load-displacement curve] as shown in FIG. 8 is obtained (the detail will be described below). As shown in FIG. 8, [the low frequency area ratio] and [the angle ratio of slope of the load-displacement curve] have a proportional relationship (linear relationship). Therefore, an impact elastic wave test is conducted with respect to a pipe to be examined (buried pipe) to obtain the above-described low frequency area ratio, and the actually measured low frequency area ratio is evaluated based on the relationship [the low frequency area ratio]-[the angle ratio of slope of the load-displacement curve], thereby making it possible to quantitatively determine the degree of deterioration of the pipe to be examined (failure state).

Note that test data of an impact elastic wave test used in the present invention may be a resonance frequency ratio, a received waveform amplitude value, a received waveform energy, a peak frequency, a frequency center-of-gravity, a waveform attenuation time, or the like in addition to the low frequency area ratio.

Here, examples of a buried pipe to which the examination method of the present invention is applied include a concrete pipe, a reinforced-concrete pipe, a ceramic pipe, a metal pipe, a resin pipe, an FRPM pipe (composite pipe of mortar and FRP), and the like. Examples of a cross-sectional shape of a buried pipe include a circular shape, an oval shape, a rectangular shape, a horse-shoe shape, and the like.

Effects of the Invention

According to the buried pipe examining method of the present invention, an impact elastic wave test is conducted to measure propagating waves in a pipe to be examined, a frequency spectrum of the propagating waves is analyzed, and at least a spectral area value in a first frequency region and a spectral area value in a second frequency region of the frequency spectrum are evaluated, thereby examining a deteriorated state of the buried pipe. Therefore, as compared to an examination method utilizing, for example, an amplitude value of elastic waves, a reduction in the counted number of elastic waves (the counted number of amplitudes larger than or equal to a predetermined value), the deterioration phenomenon type can be determined without being easily affected by a situation surrounding the buried pipe and with high accuracy.

Also, according to the buried pipe examining method of the present invention, a correlation relationship between a parameter obtained from a force-deformation relationship indicating a relationship between an external force input to a sample pipe and a deformation of the sample pipe due to the force, and impact elastic wave test data obtained by conducting an impact elastic wave test with respect to the sample pipe is previously obtained, an impact elastic wave test is, conducted with respect to a pipe to be examined (buried pipe) to collect impact elastic wave measurement data of the pipe to be examined, and the actually measured impact elastic wave measurement data is evaluated based on the correlation relationship between the parameter obtained from the force-deformation relationship and the impact elastic wave test data, thereby examining a degree of deterioration of the pipe to be examined. Therefore, the degree of deterioration can be quantitatively determined without being affected by a situation surrounding the buried pipe to be examined and with high accuracy, thereby making it possible to determine a method and a priority for reconstruction or repair.

DESCRIPTION OF REFERENCE NUMERALS

Figure 1:
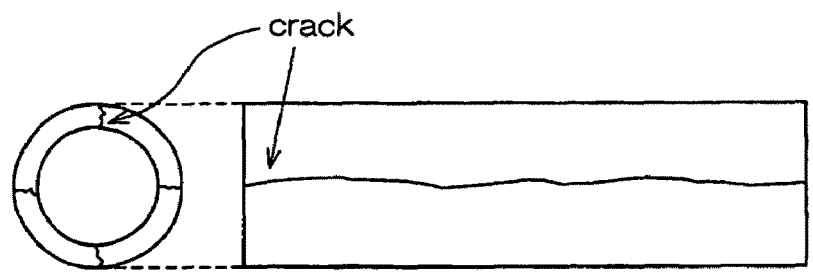
FIG. 1 is a schematic diagram of an axial crack-introduced pipe.

S1 to S5 sample buried pipe
P sample pipe
1 line load
2 high-sensitivity displacement gauge

DESCRIPTION OF THE INVENTION

Hereinafter, an embodiment of the present invention will be described with reference to the accompanying drawings.

Embodiment 1

In this embodiment, an impact elastic wave test is conducted as follows.

[Input Method]

As an input device, an impact tool, such as a hammer, a steel ball, an impulse hammer or the like, can be used. Particularly, as an input device, to reflect input information during analysis, it is desirable to impact with a constant force using an impact tool capable of measuring input information as numerical values, e.g., a Schmidt hammer, a spring, a piston or the like. Also, for example, a method of swinging a hammer, a steel ball or the like with a constant force using a Schmidt hammer, a spring, a piston or the like, or a method of dropping a steel ball or the like from a constant height, is desirable.

[Reception Method]

As a reception device, an acceleration sensor, an AE sensor, a vibration sensor, or the like can be used. As a method of setting the reception device, the device may be fixed using a tape, an adhesive or the like, or may be attached by a hand, a pressing jig or the like.

Since these input device and reception device may contact water, acidic water or basic water, it is desirable that the devices be made of a material highly resistant to corrosion, such as stainless steel or the like.

[Measurement Method]

An impulse hammer or the like is used to input elastic waves to an inner surface of a pipe. A reception device set in the pipe is used to measure waves propagating through the pipe, and a waveform is recorded by a recording device (measurement of reception data). The input position and the position of the reception device are desirably placed and separated by ¼ or more of a length of a pipe to be examined. This is because it is easy to detect a change in a vibration phenomenon of the whole pipe due to a deterioration, such as a crack or the like. It is also desirable that the input position and the reception position be set at the same relative position.

[Analysis Method]

For data of input and reception measured at the measurement positions, a frequency spectrum is drawn, taking into consideration a relationship between an input (impact side) and an output (reception side). For the frequency spectrum distribution, a spectral area value in a first frequency region (0.5 to 4 kHz) and a spectral area value in a second frequency region (0.5 to 10 kHz) are obtained. When the analysis method is employed, an impact force (input information) of an impulse hammer needs to be converted into a numerical value.

Here, for example, the frequency spectrum in view of the relationship between an input and an output is represented by $H(f)=B(f)/A(f)$ where $A(f)$ represents a Fourier spectrum of the input, $B(f)$ represents a Fourier spectrum of the output, and $H(f)$ represents a transfer function (frequency response function). $H(f)$ draws a distribution of the frequency spectrum.

EXAMPLE 1

A specific example of the present invention will be described.

[Preparation of Samples]

A concrete hume pipe (manufactured by Nippon Hume Corporation) having a nominal diameter of 250 mm (pipe length: 2 m) and conforming to the standards of JIS A 5372 (Shape B, Type 1) was used to prepare the following samples.

Sample S1: Non-treated pipe (pipe wall thickness: average 28 mm). Note that the pipe wall thickness was measured in the vicinity of end surfaces of the pipe (10 points for each end; a total of 20 points) using a vernier caliper.

Sample S2: Axial Crack-Introduced Pipe

A load test machine capable of applying a line load to a sample was used to generate four cracks (crack width=0.15 mm) in an axial direction (see FIG. 1). Note that the number of cracks occurring in an end surface (inner and outer surfaces) was confirmed by visual inspection.

Figure 2:
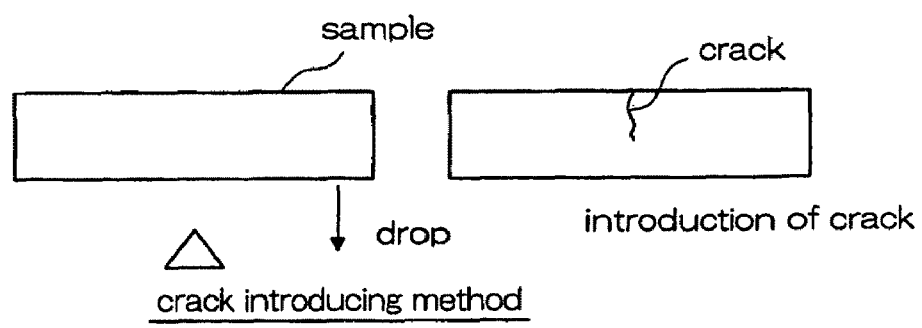
FIG. 2 is a diagram schematically showing a method for introducing a circumferential crack which is employed in an example of the present invention.
Figure 3:
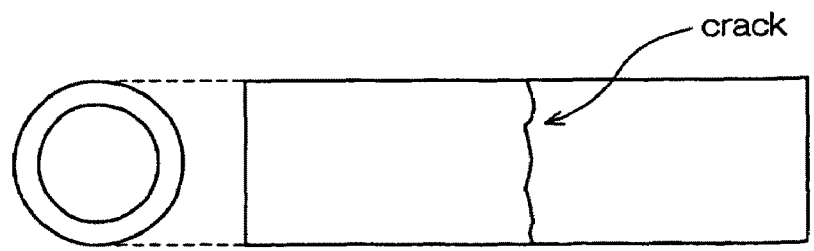
FIG. 3 is a schematic diagram of a circumferential crack-introduced pipe.
Figure 4:
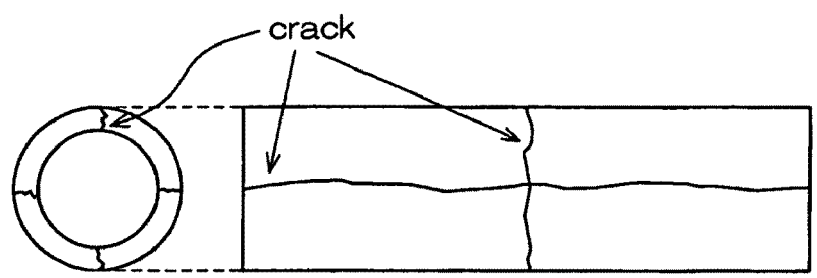
FIG. 4 is a schematic diagram of an axial+circumferential crack-introduced pipe.
Figure 5:
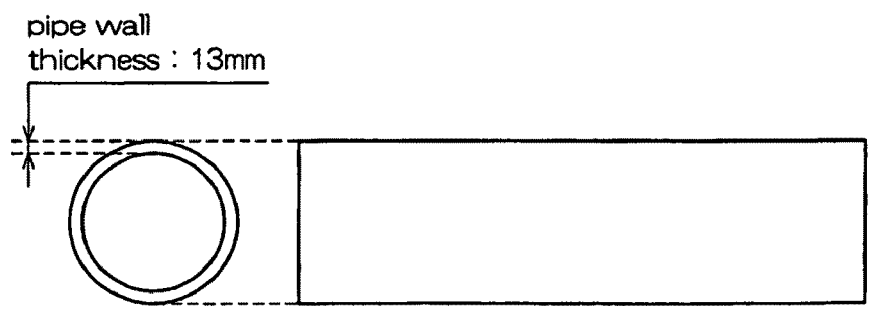
FIG. 5 is a schematic diagram of a wall thickness-reduced pipe.

Sample S3: Circumferential Crack-Introduced Pipe
   A crack having a crack width of 1.3 mm (see FIG. 3) was introduced using an introduction method as shown in FIG. 2. Note that the crack width was measured in pipe circumferences while being enlarged by a loupe with scale (average value of five points).
Sample S4: Axial+Circumferential Crack-Introduced Pipe
   After axial cracks were introduced in a manner similar to that for sample S2, circumferential cracks were introduced in a manner similar to that for sample S3 (see FIG. 4).
Sample S5: Pipe Wall Thickness-Reduced Pipe
   By special forming, the same outer diameter as that of the non-treated pipe was provided, and the inner diameter was increased so that the average pipe wall thickness was 13 mm (see FIG. 5). Note that the pipe wall thickness was measured in the vicinity of end surfaces of the pipe (10 points for each end; a total of 20 points) using a vernier caliper.
A list of the samples is shown in Table 1 below.

TABLE 1

| Sample S1 | Sample S2 | Sample S3 | Sample S4 | Sample S5 |
| --- | --- | --- | --- | --- |
| Non-treated pipe | Axial crack-introduced pipe | Circumferential crack-introduced pipe | Axial + circumferential crack-introduced pipe | Wall thickness-reduced pipe |

Figure 6:
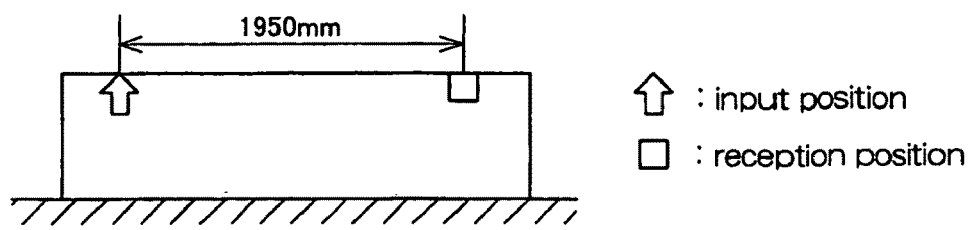
FIG. 6 is a diagram showing an arrangement of measurement devices in a sample.
Figure 7:
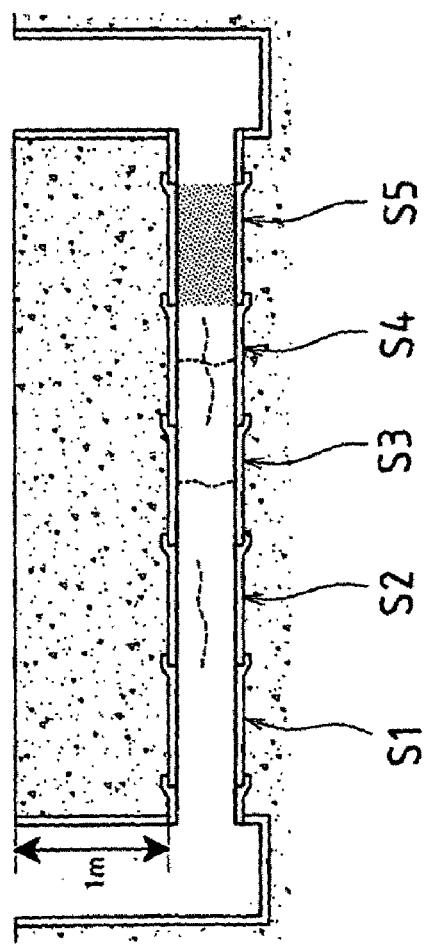
FIG. 7 is a diagram schematically showing conditions under which a sample is buried in an example of the present invention.

[Input and Reception Positions]
An input device and a reception device were placed at positions indicated in FIG. 6 to input elastic waves and receive propagating waves.
[Devices Used]
Input device: Impulse hammer
Reception device: Vibration sensor GH-313A (manufactured by Keyence Corporation). A cylindrical material having a diameter of 10 mm and a height of 15 mm was screwed into an external thread portion.
Amplifier for reception: GA-245 manufactured by Keyence Corporation
Data logger (recording device): NR-2000 manufactured by Keyence Corporation
[Measurement Conditions]
Assuming real pipelines, measurement was conducted with respect to samples S1 to S5 described above, which were buried under conditions as shown in FIG. 7.
[Data Analysis]
An input Fourier spectrum A(f) was obtained from an impact force of the input device (impulse hammer), and an output Fourier spectrum B(f) was obtained from waveform data of propagating waves received and recorded by the reception device. The input Fourier spectrum A(f) and the output Fourier spectrum B(f) were used to obtain a transfer function (frequency response function) H(f) (H(f)=B(f)/A(f)) between an input and an output. A frequency spectrum was drawn for each of samples S1 to S5, taking the relationship between an input and an output into consideration.

Figure 8:
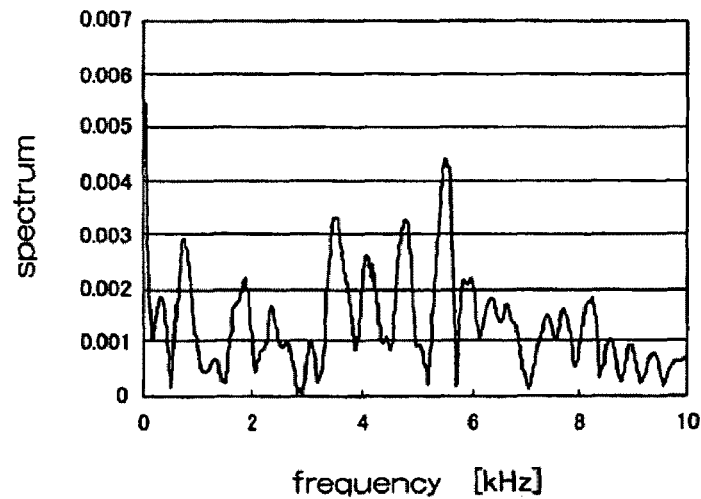
FIG. 8 is a distribution graph of a frequency spectrum of a non-treated pipe (sound pipe).
Figure 9:
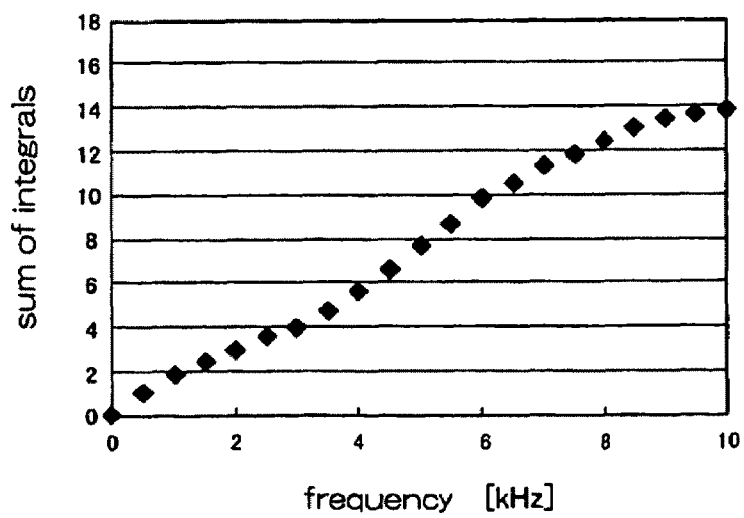
FIG. 9 is a graph showing the sum of integrals of the frequency spectrum of FIG. 8.
Figure 10:
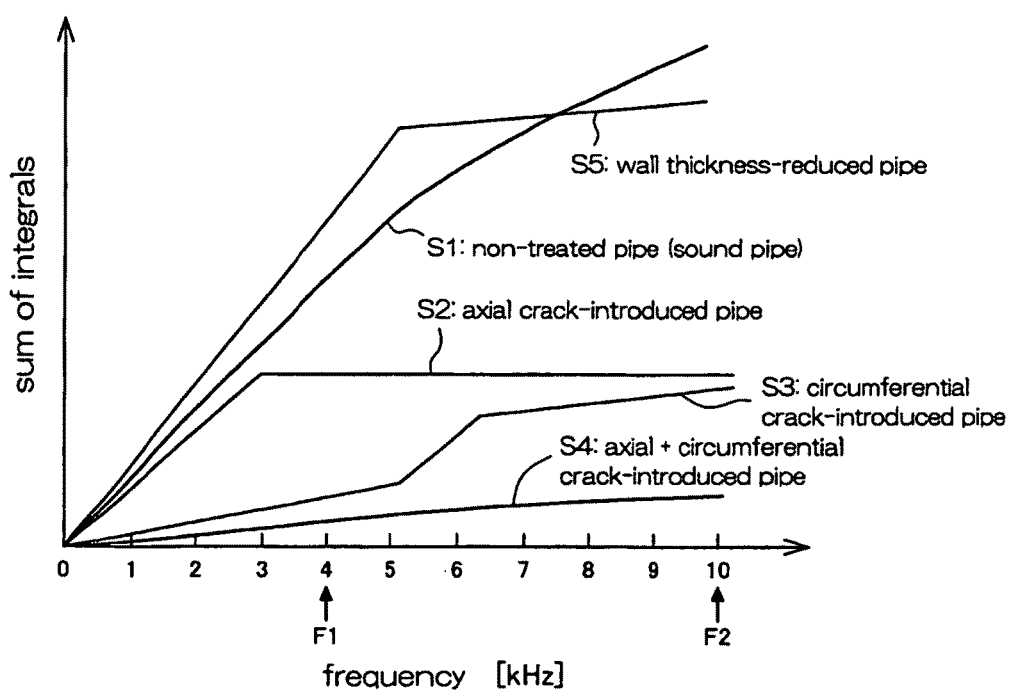
FIG. 10 is a graph showing the sums of integrals of frequency spectra of a plurality of types of pipes having different states.

Of these samples, a distribution graph of the frequency spectrum of sample S1 (non-treated pipe (sound pipe)) is shown in FIG. 8. Also, for the frequency spectrum of sample S1, an integral (spectral area value) was calculated every a small frequency region (0.5 kHz). The sum of the integrals obtained by successively summing the integrals was plotted on a graph where the frequency is a parameter, to obtain a graph as shown in FIG. 9. Further, using a similar technique, the sum of integrals was obtained for the frequency spectrum of each of samples S2 to S5, and frequency-sum of integrals graphs were produced. When the sums of integrals of all the samples S1 to S5 are plotted on the same graph, a tendency appears as indicated in FIG. 10. The details have been described above and will not be here described. Note that the graph of FIG. 10 is a model of changes in the sum of integrals of each of samples S1 to S5.

Figure 11:
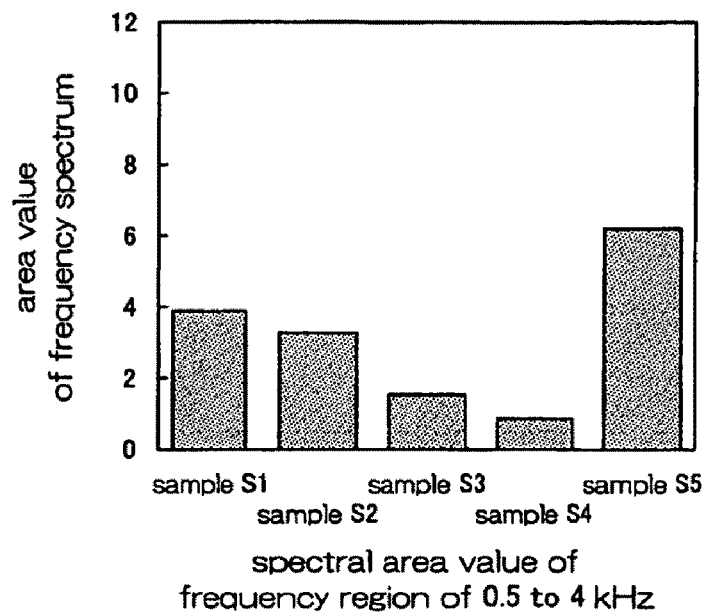
FIG. 11 is a graph showing results of an example of the present invention, indicating a spectral area value in a frequency region of 0.5 to 4 kHz of each sample.
Figure 12:
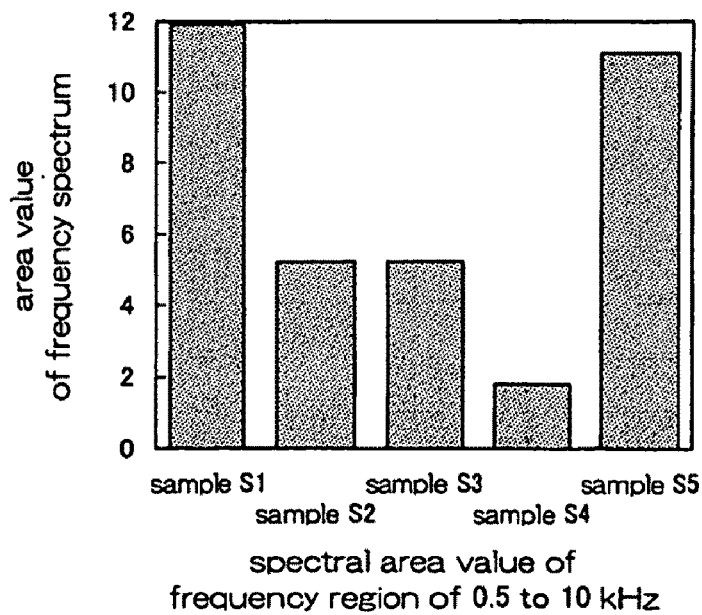
FIG. 12 is a graph showing results of an example of the present invention, indicating a spectral area value in a frequency region of 0.5 to 10 kHz of each sample.

In this example, for the frequency spectrum of each of samples S1 to S5, a spectral area value in a first frequency region of 0.5 to 4 kHz and a spectral area value in a second frequency region of 0.5 to 10 kHz are calculated. The results are shown in FIG. 11 and FIG. 12, respectively.

Next, the spectral area value in the first frequency region of 0.5 to 4 kHz is evaluated (hereinafter referred to as a first evaluation). Specifically, the "non-treated pipe (sound pipe)" is used as a reference. The spectral area value is considered to be "large" when it is larger than that of the "non-treated pipe", "intermediate" when it is about the same as or slightly smaller than that of the "non-treated pipe", and "small" when it is extremely smaller than that of the "non-treated pipe". The result of the evaluation is shown in Table 2 below.

Further, the spectral area value in the second frequency region of 0.5 to 10 kHz is evaluated (hereinafter referred to as a second evaluation). Specifically, the "non-treated pipe (sound pipe)" is used as a reference. The spectral area value is considered to be "large" when it is about the same as or slightly smaller than that of the "non-treated pipe", "intermediate" when it is smaller than that of the "non-treated pipe", and "small" when it is extremely smaller than that of the "non-treated pipe". The results of the evaluation are shown in Table 2 below.

TABLE 2

| | Sample S1 Non-treated pipe | Sample S2 Axial crack-introduced pipe | Sample S3 Circumferential crack-introduced pipe | Sample S4 Axial + circumferential crack-introduced pipe | Sample S5 Wall thickness-reduced pipe |
| --- | --- | --- | --- | --- | --- |
| Spectral area value in frequency region of 0.5 to 4 kHz | Reference (intermediate) | intermediate | small | small | large |
| Spectral area value in frequency region of 0.5 to 10 kHz | Reference (large) | intermediate | intermediate | small | large |

According to the results of Table 2, the type of a deterioration phenomenon in each of samples S1 to S5 can be specified. Specifically, when the first evaluation is "intermediate" and the second evaluation is "intermediate", the deterioration phenomenon type can be determined to be the "axial crack". When the first evaluation is "small" and the second evaluation is "intermediate", the deterioration phenomenon type can be determined to be the "circumferential crack". When the first evaluation is "small" and the second evaluation is "small", the deterioration phenomenon type can be determined to be the "axial+circumferential crack". When the first evaluation is "large" and the second evaluation is "large", the deterioration phenomenon type can be determined to be the "pipe wall thickness reduction". Note that, in the case of the reference "non-treated pipe (sound pipe)", the first evaluation is "intermediate" and the second evaluation is "large".

Therefore, an impact elastic wave test is previously conducted with respect to a non-treated pipe (sample pipe) to calculate and record a spectral area value in the first frequency region of 0.5 to 4 kHz and a spectral area value in the second frequency region of 0.5 to 10 kHz. For a pipe to be examined (buried pipe), an impact elastic wave test is conducted to obtain a frequency spectrum, and a spectral area value in each of the frequency regions of 0.5 to 4 kHz and 0.5 to 10 kHz is obtained from the frequency spectrum. The magnitudes of the actually measured spectral area values are subjected to the first and second evaluations (two steps) with reference to the previously recorded spectral area values (spectral area values of the non-treated pipe (reference)). Thereby, it is possible to specify the type of a deterioration phenomenon in the pipe to be examined.

Note that thresholds which are criteria for determining "large", "intermediate", and "small" in the first and second evaluations may be obtained based on a graph as shown in FIG. 10 which is produced by previously conducting an impact elastic wave test for each of samples S1 to S5.

Although, in the above-described example, the first frequency region for obtaining a spectral area is 0.5 to 4 kHz, and the second frequency region is 0.5 to 10 kHz, the present invention is not limited to this. The present invention can also be carried out when the start point of the first frequency region is in the range of 0 to 2.5 kHz and the end point is in the range of 3 to 5.5 kHz, and the start point of the second frequency region has the same value as that of the first frequency region and the end point is in the range of 7 to 10 kHz.

Also, the number of frequency regions in which a spectral area value is obtained is not limited to two (i.e., the above-described first and second frequency regions), and may be three or more.

Next, for another embodiment of the present invention, a specific example will be described with reference to the drawings.

Embodiment 2

EXAMPLE 2

Firstly, a sample pipe and each test method used in this example will be described.

Sample Pipe

A concrete hume pipe (manufactured by Nippon Hume Corporation) having a nominal diameter of 250 mm (pipe length: 2 m) and conforming to the standards of JIS A 5372 (Shape B, Type 1) was used.

Loading Test with Line Load (External Pressure Test)

Figure 13:
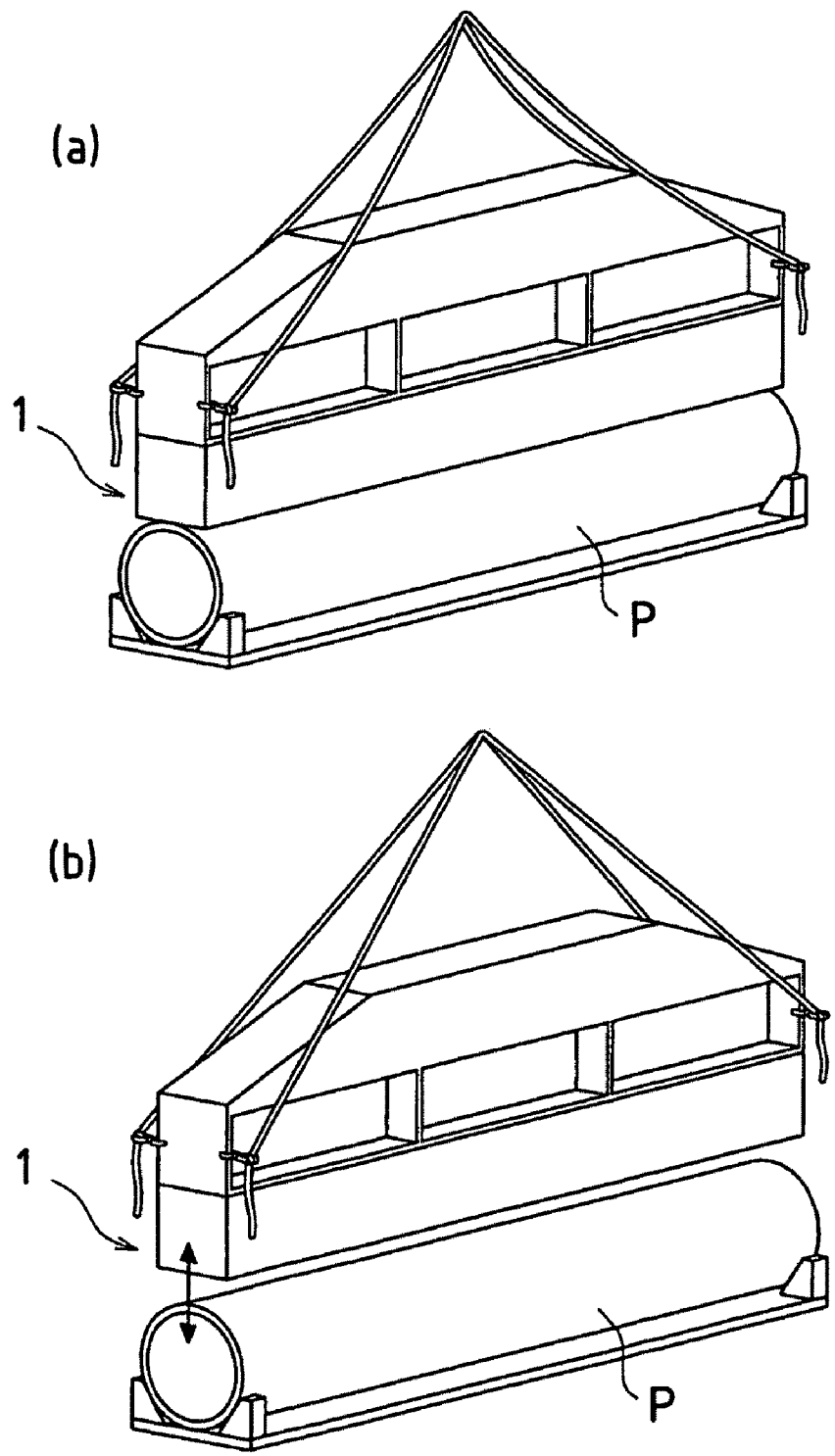
FIG. 13 is a diagram for describing a loading test method in another example of the present invention.
Figure 14:
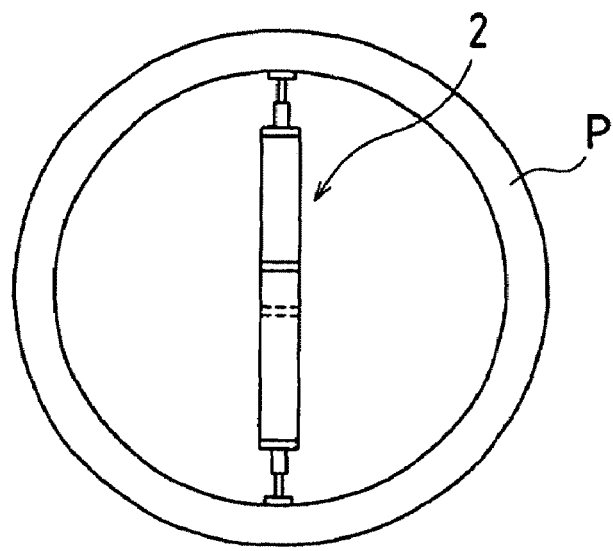
FIG. 14 is a diagram showing an arrangement of a high-sensitivity displacement gauge in a sample pipe.

As shown in FIGS. 13(a) and (b), a line load 1 having a shape extending along an axial direction of a sample pipe P was placed on the sample pipe P from the top. Also, as shown in FIG. 14, a high-sensitivity displacement gauge 2 was placed inside the sample pipe P along a perpendicular direction, to measure a displacement of the sample pipe P when the line load 1 was applied to the sample pipe P, thereby obtaining a load-displacement curve.

Here, the placement of the line load 1 was not continuously conducted. The line load 1 was removed every a predetermined step (see FIG. 13(b)), i.e., the line load 1 was intermittently placed. Specifically, the line load 1 was once removed in an elastic region until a crack occurred after the start of loading. An impact elastic wave test described below was then conducted before the line load 1 was placed again. Next, the line load 1 was removed when a crack occurred. An impact elastic wave test was then conducted before the line load 1 was placed again. After a crack occurred, every time when displacements measured by the high-sensitivity displacement gauge 2 reached [displacement=2.4 mm], [displacement=4.3 mm], [displacement=6.3], [displacement=9.4], [displacement=12.6], and [displacement=20.3], the line load 1 was removed and an impact elastic wave test described below was conducted before the line load 1 was placed again.

Impact Elastic Wave Test

In this example, an impact elastic wave test was conducted as follows.

[Input and Reception Positions]

Figure 15:
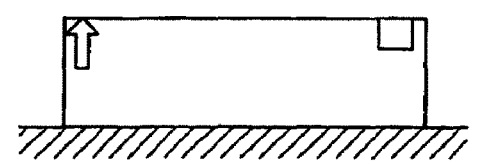
FIG. 15 is a diagram showing an arrangement of measurement devices in a pipe when an impact elastic wave test is conducted.
Figure 16:
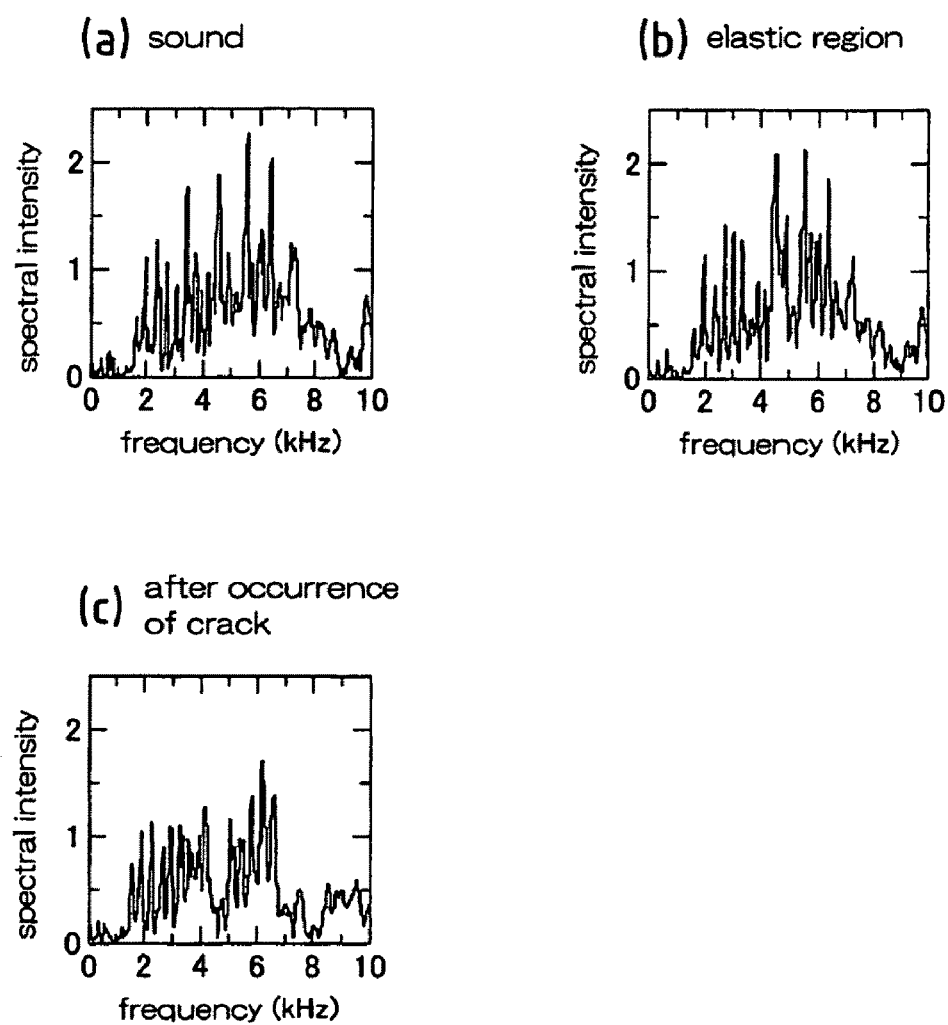
FIG. 16 is a diagram showing a frequency spectrum distribution based on waveform data of propagating waves measured at each measurement point in a load measurement process.
Figure 17:
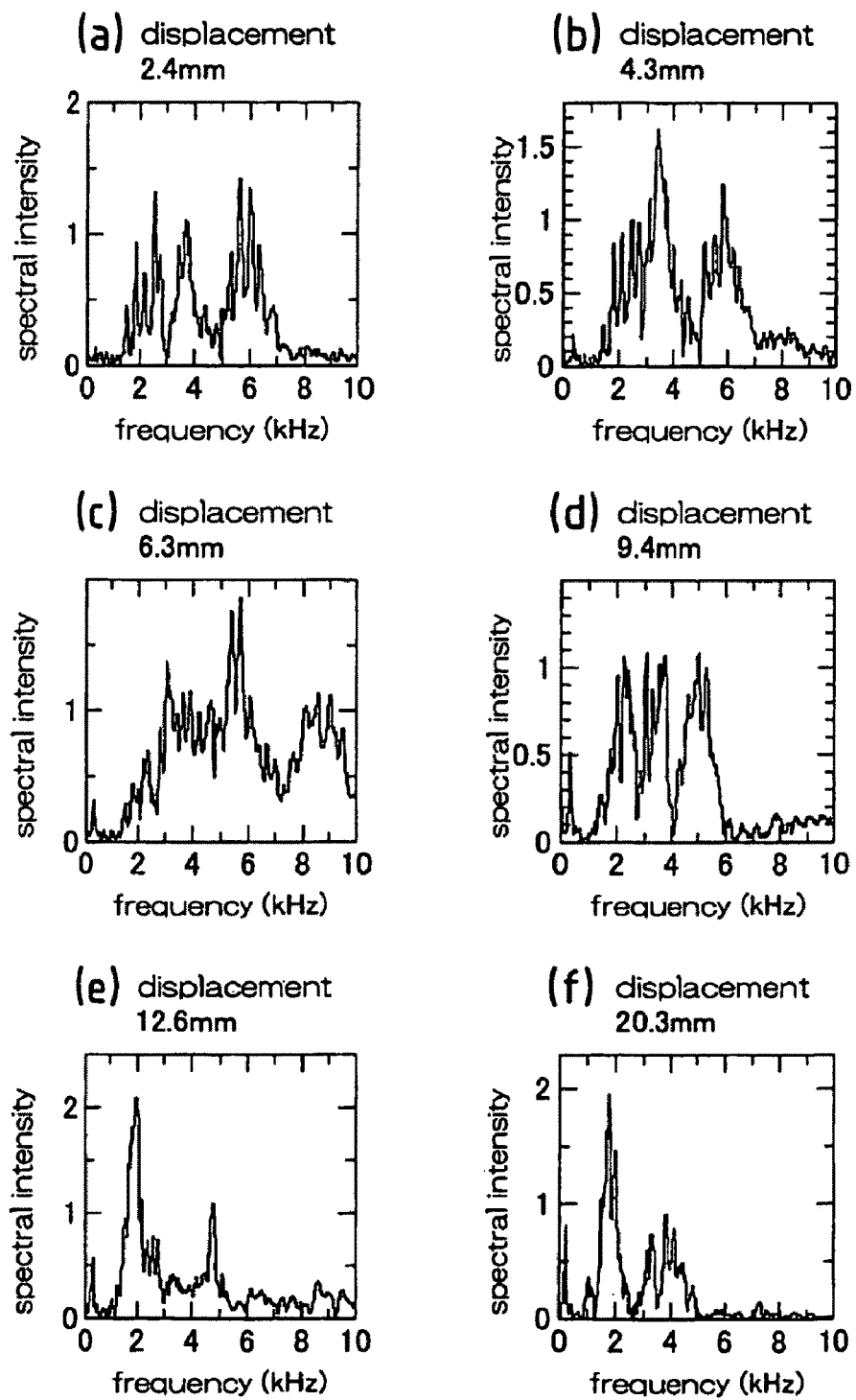
FIG. 17 is a diagram showing a similar frequency spectrum distribution.

An input device and a reception device were placed at positions indicated in FIG. 15 to input elastic waves and receive propagating waves.

[Devices Used]

Input device: Impulse hammer

Reception device: Vibration sensor GH-313A (manufactured by Keyence Corporation). A cylindrical material having a diameter of 10 mm and a height of 15 mm was screwed into an external thread portion. Note that the reception device was set by pressing with a hand.

Amplifier for reception: GA-245 manufactured by Keyence Corporation

Data logger (recording device): NR-2000 manufactured by Keyence Corporation

[Calculation of Frequency Area]

An input Fourier spectrum A(f) was obtained from an impact force of the input device (impulse hammer), and an output Fourier spectrum B(f) was obtained from waveform data of propagating waves received and recorded by the reception device. The input Fourier spectrum A(f) and the output Fourier spectrum B(f) were used to obtain a transfer function (frequency response function) H(f) (H(f)=B(f)/A(f)) between an input and an output. A frequency spectrum was drawn at each measurement point, taking into consideration the relationship between an input and an output. The frequency spectrum distributions are shown in FIGS. 16(a) to 16(c) and FIGS. 17(a) to 17(f).

Figure 18:
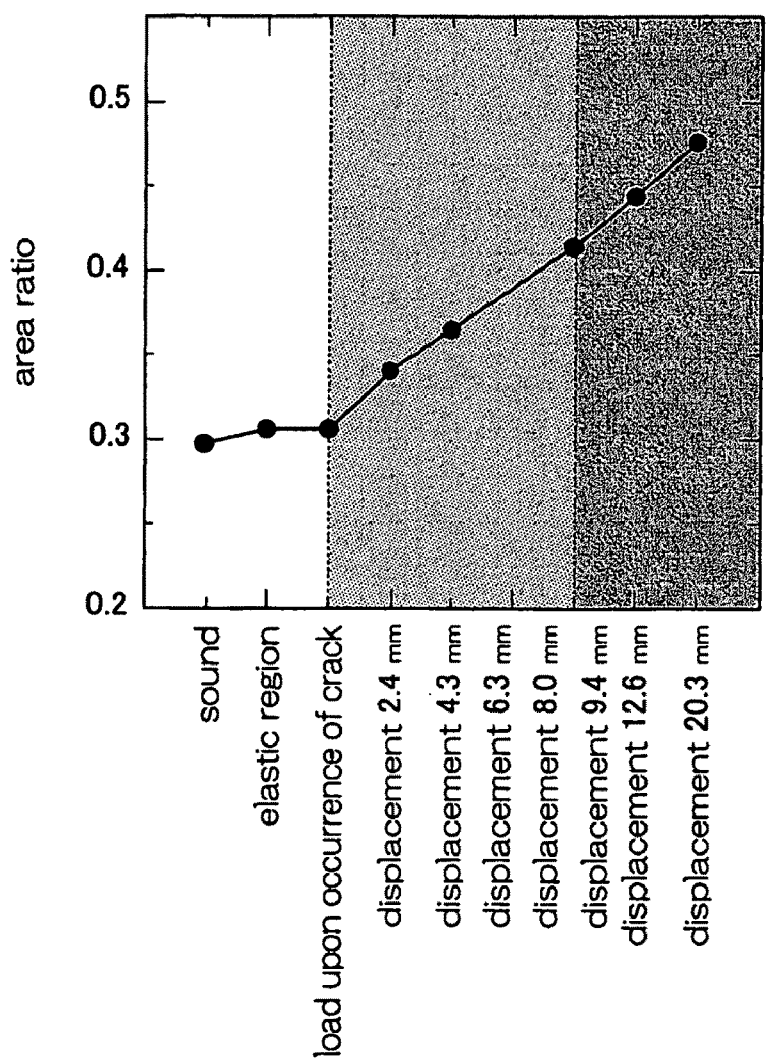
FIG. 18 is a graph showing a relationship between the result of measurement at each measurement point in a loading test and a low frequency area ratio.

Next, a frequency region of 0 to 5 kHz and a frequency region of 0 to 10 kHz in the frequency spectrum distribution obtained at each measurement point were obtained. Using these, a low frequency area ratio was calculated in accordance with an expression described below. A relationship between the calculated low frequency area ratio and the result of measurement at each measurement point in the loading test is shown in Table 3 below and FIG. 18.

Low frequency area ratio=[the area of low frequency components (0 to 5 kHz)]/[the area of predetermined-region components (0 to 10 kHz)]

TABLE 3

| | Conditions | Frequency area ratio | Angle ratio of slope at each measurement point of load-displacement curve | State of pipe State | Remaining strength ratio (%) | |
|---|---|---|---|---|---|---|
| Sound | Sound | 0.3 | 1 | Sound | 100 | |
| | Elastic region | 0.31 | 1 | Sound | 100 | |
| | Crack occurring load | 0.31 | 1.01 | Occurrence of crack | 100 | ← Crack load |
| Crack | Displacement 2.4 mm | 0.34 | 0.84 | Progression of crack | 70.0 | |
| | Displacement 4.3 mm | 0.36 | 0.81 | Almost saturation of increase in load | 50.0 | |
| | Displacement 6.3 mm | 0.38 | 0.72 | Almost saturation of increase in load | 30.0 | |
| | Displacement 9.4 mm | 0.41 | 0.64 | Almost saturation of increase in load | 0 | ← Maximum load |
| Break | Displacement 12.6 mm | 0.45 | 0.51 | Break point | 0 | |
| | Displacement 20.3 mm | 0.47 | 0.26 | Break point | 0 | |

Correlation between Frequency Area and Load-Displacement Curve

As a factor for a frequency spectrum obtained by an impact elastic wave test, the above-described low frequency area ratio (=[the area of low frequency components (0 to 5 kHz)]/[the area of predetermined-region components (0 to 10 kHz)]) is used.

Also, a factor used for a load-displacement curve is assumed to be an angle of slope at each measurement point of the load-displacement curve (apparent rigidity). In this example, an angle ratio of slope at each measurement point of the load-displacement curve is used.

Figure 19:
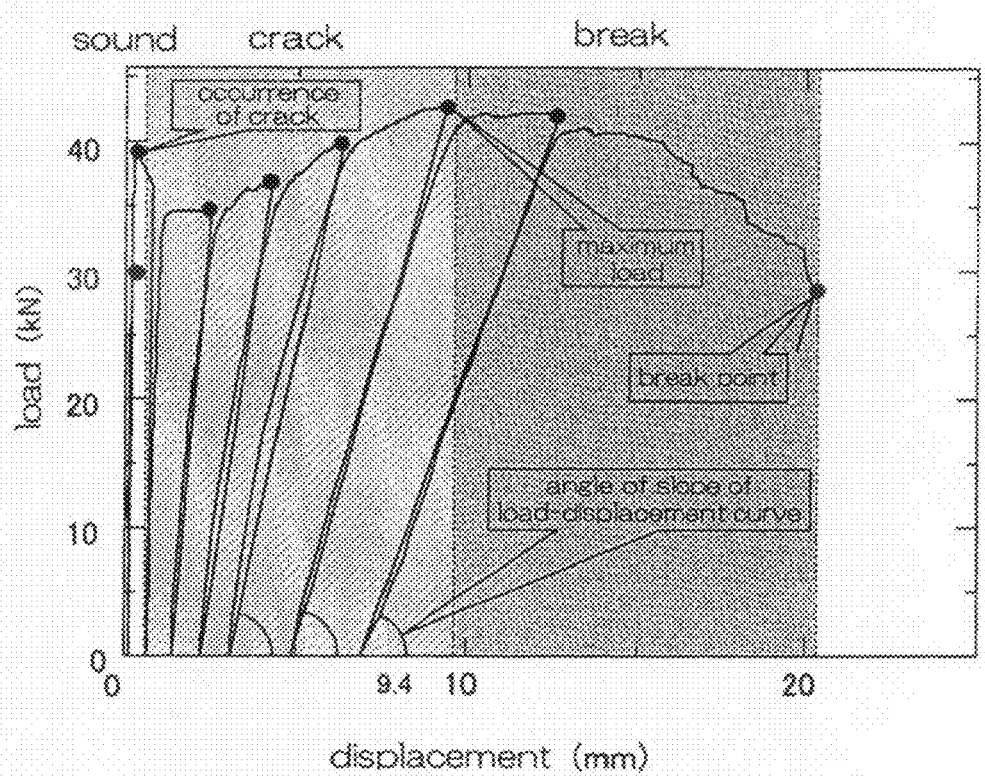
FIG. 19 is a diagram showing a load-displacement curve.

Here, the angle ratio of slope at each measurement point of the load-displacement curve is defined as [the angle of slope at a measurement point]/[the angle of slope at a crack occurring point]. Also, the angle of slope at a measurement point refers to an angle of slope of a straight line drawn through the measurement point in a load-displacement curve of FIG. 19.

Figure 20:
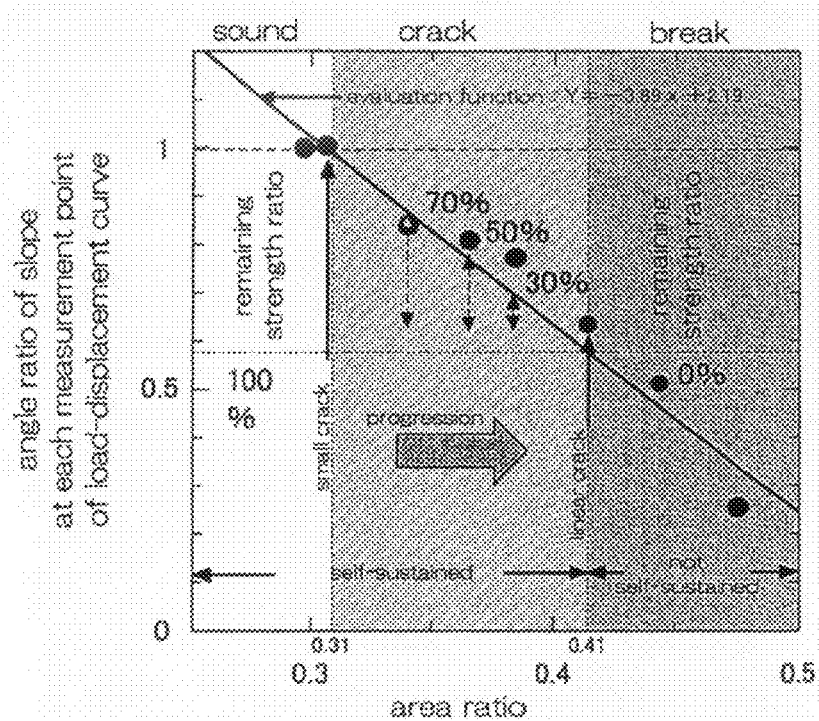
FIG. 20 is a graph showing a relationship between a low frequency area ratio and an angle ratio of slope at each measurement point in a load-displacement curve.

The low frequency area ratio of the frequency spectrum distribution (horizontal axis) and the angle ratio of slope at each measurement point of the load-displacement curve (vertical axis) that are obtained as described above were plotted at each measurement point. As a result, as shown in FIG. 20, it was found that the frequency area ratio and the angle ratio of slope at each measurement point of the load-displacement curve have a proportional relationship (linear relationship). Note that the slope of the graph of FIG. 20 is $y=-3.89x+2.19$ where x represents the frequency area ratio, and y represents the angle ratio of slope at each measurement point of the load-displacement curve.

Assuming that a frequency area ratio (=0.31) when a crack occurs is 100% and a frequency area ratio (=0.41) at a maximum load is 0%, a progression state of deterioration of a pipe is represented by a remaining strength ratio: $A=-1000x+410$ where x represents the frequency area ratio and A represents the remaining strength ratio (%).

Thus, a low frequency area ratio obtained in an impact elastic wave test can be related to a state of a pipe (remaining strength ratio). Therefore, for a pipe to be examined (buried pipe), a low frequency area ratio is obtained from a frequency-spectrum distribution obtained by conducting an impact elastic wave test, and the actually measured low frequency area ratio (x) is converted into a remaining strength ratio (%) using the above-described remaining strength estimating function ($A=-1000x+410$), thereby making it possible to determine the degree of deterioration of the pipe to be examined in a numerical value. Thereby, a method and a priority for reconstruction or repair can be determined.

Process of Determining Degree of Deterioration

Figure 21:
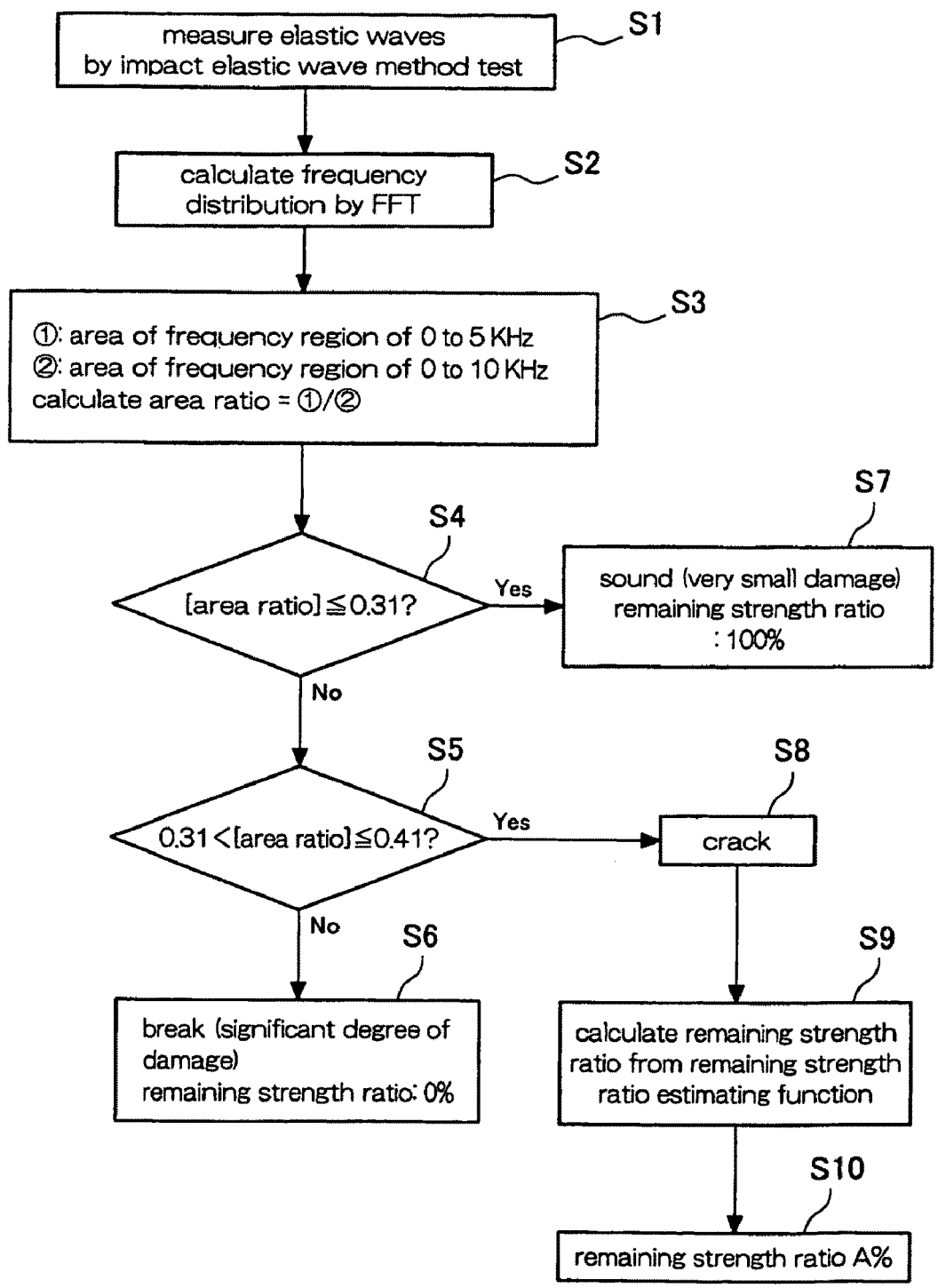
FIG. 21 is a flowchart showing an exemplary deterioration degree determining process.

A specific example of a deterioration degree determining process will be described with reference to a flowchart of FIG. 21. Note that, in this example, determination is performed using FIG. 20, Table 3 and the remaining strength estimating function ($A=-1000x+410$) described above.

Step S1: Waves propagating through a pipe to be examined are measured using the measurement method of the above-described impact elastic wave test. Note that the measurement conditions and the like are assumed to be the same as those for the above-described sample pipe P.

Step S2: The measured waveform data is subjected to FFT to calculate a frequency spectrum distribution. Note that the method of calculating the frequency spectrum distribution is the same as that for the above-described sample pipe P.

Step S3: From the frequency spectrum distribution calculated in step 2, a frequency region of 0 to 5 kHz and a frequency region of 0 to 10 kHz in the frequency spectrum distribution are obtained. These are used to calculate a low frequency area ratio (=[the area of low frequency components (0 to 5 kHz)]/[the area of predetermined-region components (0 to 10 kHz)].

Step S4: It is determined whether or not the low frequency area ratio calculated in step S3 is 0.31 or less ($\leq 0.31$). When the low frequency area ratio is 0.31 or less, it is determined that the pipe is sound (remaining strength ratio=100%) (step S7). On the other hand, when the low frequency area ratio exceeds 0.31, the process goes to step S5.

Step S5: When the low frequency area ratio is 0.31<[the low frequency area ratio]≦0.41, it is determined that a crack occurs (step S8), and the remaining strength estimating function (A=−1000x+410) is used to calculate a remaining strength ratio A (%) (steps S9 and S10). On the other hand, when the low frequency area ratio exceeds 0.41 (0.41<[the low frequency area ratio]), it is determined that pipe is broken (remaining strength=0%) (step S6).

As described above, in this example, the state of a pipe to be examined (buried pipe) is determined using a numerical value (percentage), so that the degree of deterioration of the pipe to be examined can be correctly detected. Thereby, for example, when a crack occurs in the pipe to be examined, the progression state of deterioration in strength due to the crack can be represented by a numerical value (%). Therefore, a clear criterion used to determine a method and a priority for reconstruction or repair is obtained.

Although, in the above-described examples, a high-sensitivity displacement gauge is provided in a sample pipe so as to draw a load-displacement curve, the present invention is not limited to this. A strain gauge may be attached to a sample pipe so as to draw a stress-strain curve. A force-deformation curve for a sample pipe may be drawn in other external pressure tests.

Although, in the above-described examples, a frequency area ratio is employed as test data for an impact elastic wave test, the present invention is not limited to this. Test data, such as a resonance frequency, a received-waveform amplitude value, a received-waveform energy, a peak frequency, a frequency center-of-gravity, a waveform attenuation time, or the like, may be employed.

Thus, the examination method of the present invention can be used to determine the type of a deterioration phenomenon occurring in a buried pipe, and quantitatively determine the degree of deterioration.

The present invention can be embodied and practiced in other different forms without departing from the spirit and essential characteristics thereof. Therefore, the above-described embodiments are considered in all respects as illustrative and not restrictive. The scope of the invention is indicated by the appended claims rather than by the foregoing description. All variations and modifications falling within the equivalency range of the appended claims are intended to be embraced therein.

Note that this application claims priority on Patent Application Nos. 2004-217832 and 2004-217833 filed in Japan on Jul. 26, 2004, the entire contents of which are hereby incorporated by reference. Also, the documents cited herein are hereby incorporated by reference in their entirety.

INDUSTRIAL APPLICABILITY

The examination method of the present invention can be effectively used to determine the types of deterioration phenomena in elemental zones constituting an exploration range and correctly detect the progression degrees of deterioration in the elemental zones, so as to prioritize repair/reconstruction works and determine work methods for a buried pipe in a sewer pipeline, an agricultural pipeline, or the like.

The invention claimed is:

1. A method for examining a deteriorated state of a buried pipe from inside of the pipe, wherein a correlation relationship between a parameter obtained from a force-deformation relationship indicating a relationship between a force externally input to a sample pipe and a deformation of the sample pipe due to the force, and impact elastic wave test data obtained by conducting an impact elastic wave test with respect to the sample pipe is previously obtained, an impact elastic wave test is conducted with respect to a pipe to be examined to collect impact elastic wave measurement data of the pipe to be examined, and the actually measured impact elastic wave measurement data is evaluated based on the correlation relationship between the parameter obtained from the force-deformation relationship and the impact elastic wave test data, thereby quantitatively determining a degree of deterioration of the pipe to be examined.

2. The buried pipe examining method according to claim 1, wherein a load-displacement curve or a stress-strain curve is used as the force-deformation relationship of the sample pipe.

3. The buried pipe examining method according to claim 1, wherein an angle ratio of slope of a load-displacement curve or a stress-strain curve is used as the parameter obtained from the force-deformation relationship.

4. The buried pipe examining method according to claim 1, wherein an impact elastic wave test is conducted to measure propagating waves in a pipe, a frequency spectrum of the propagating waves is analyzed, and an area ratio of low frequency components to a predetermined frequency region of the frequency spectrum is used as the impact elastic wave test data and the actually measured impact elastic wave data.

* * * * *